US008821921B2

(12) United States Patent
Lyftogt

(10) Patent No.: US 8,821,921 B2
(45) Date of Patent: Sep. 2, 2014

(54) VITAMIN D3 FOR THE TRANSDERMAL TREATMENT OF PAIN AND INFLAMMATION

(71) Applicant: Anzamed International Limited, Auckland (NZ)

(72) Inventor: Jan Anne Lyftogt, Lyttelton (NZ)

(73) Assignee: Anzamed International Limited, Auckland (NZ)

( * ) Notice: Subject to any disclaimer, the term of this patent is extended or adjusted under 35 U.S.C. 154(b) by 0 days.

(21) Appl. No.: 13/783,550

(22) Filed: Mar. 4, 2013

(65) Prior Publication Data
US 2013/0177622 A1    Jul. 11, 2013

Related U.S. Application Data

(62) Division of application No. 13/144,807, filed as application No. PCT/NZ2009/000167 on Aug. 13, 2009, now abandoned.

(30) Foreign Application Priority Data

Jan. 16, 2009 (NZ) .......................... 574231
Mar. 6, 2009 (NZ) .......................... 575379

(51) Int. Cl.
A61F 13/02 (2006.01)
A61K 9/70 (2006.01)
A61K 31/593 (2006.01)

(52) U.S. Cl.
USPC ........................................... 424/449; 514/167

(58) Field of Classification Search
None
See application file for complete search history.

(56) References Cited

U.S. PATENT DOCUMENTS 5,318,960 A * 6/1994 Toppo ........................... 514/159

* cited by examiner

*Primary Examiner* — Carlos Azpuru
(74) *Attorney, Agent, or Firm* — Florek & Endres PLLC

(57) ABSTRACT

The use of vitamin D3 for the manufacture of a medicament for the transdermal treatment of neurogenic inflammation and neuropathic pain (including peripheral neuropathic pain); also a method for the relief of neurogenic inflammation and neuropathic pain using this medicament.

6 Claims, 3 Drawing Sheets

VITAMIN D3 FOR THE TRANSDERMAL TREATMENT OF PAIN AND INFLAMMATION

This application is a divisional application of U.S. Ser. No. 13/144,807, filed Jul. 15, 2011, which in turn is a U.S. National Stage filing under 35 U.S.C. §371 of International Application No. PCT/NZ2009/000167, filed Aug. 13, 2009, which in turn claims priority to New Zealand Patent Application No. 574231, filed Jan. 16, 2009 and also to New Zealand Patent Application No. 575379, filed Mar. 6, 2009.

FIELD OF THE INVENTION

The present invention relates to a medicament for the relief of pain and inflammation, in particular neurogenic inflammation and neuropathic pain. The medicament of the present invention has been found to be especially effective in the relief of peripheral neuropathic pain.

BACKGROUND OF THE INVENTION

Neurogenic inflammation is inflammation of the nerves which is actually caused by the nerves, in the sense that it is caused by the pro-inflammatory neuropeptides released by the nerves when the nerves are irritated, damaged, or injured. The neurogenic inflammation causes the neuropathic pain. Peripheral neuropathic pain is neuropathic pain experienced in the distribution of the peripheral nervous system, i.e. outside the central nervous system (brain and spinal cord). Typical sites for peripheral neuropathic pain are the heels/hands/feet/elbows/knees.

Neurogenic inflammation, and the resulting neuropathic pain, typically are difficult to treat and often respond poorly to standard pain treatments. Treatments typically used for neurogenic inflammation and neuropathic pain (including peripheral neuropathic pain) include non-steroidal anti-inflammatory drugs, painkillers, anticonvulsant drugs, antidepressant drugs, electrical nerve stimulation, and corticosteroid/local anaesthetic injections; however, none of these treatments reliably reduces the pain in a majority of cases, and in addition may have undesirable side-effects.

DISCLOSURE OF THE INVENTION

An object of the present invention is the provision of a medicament capable of providing a convenient, safe and effective relief for neurogenic inflammation and neuropathic pain (including peripheral neuropathic pain), with minimal risk of undesirable side-effects.

The present invention provides the use of vitamin D3 for the manufacture of a medicament for the transdermal treatment of neurogenic inflammation and neuropathic pain (including peripheral neuropathic pain).

The present invention further provides a method for the relief of neurogenic inflammation and neuropathic pain (including peripheral neuropathic pain) by the transdermal application of a medicament including vitamin D3.

Preferably, the medicament of the present invention includes a carrier medium suitable for transdermal application, in which vitamin D3 is dispersed or dissolved. It should be noted that vitamin D3 is fat soluble. Vitamin D3 is commercially available either as a powder or dissolved in a plant oil; in either form it can be mixed into the carrier medium. It is envisaged that suitable carrier mediums for transdermal application would include aqueous-based creams, massage oils, ointments, gels, pessaries/suppositories, patches, and impregnated bandages or other sheet material, e.g. insoles for footwear.

It should be noted that, as used herein, the term "vitamin D3" means cholecalciferol, (i.e. the pro-hormone form of vitamin D3) as opposed to the metabolically active form, calcitriol.

The preferred range of concentration of the vitamin D3 in the medicament is in the range 5000 IU/gram to 100,000 IU/gram; a concentration of 40,000 IU/gram has been found particularly effective. (IU is an abbreviation of "International Unit").

Vitamin D3 is of course known as a vitamin necessary for bone health, although the recommended daily intake of vitamin D3 is currently a matter of debate.

Over the last 10 years, studies carried out in USA and UK have indicated that people suffering from persistent, non-specific musculoskeletal pain syndromes resistant to normal forms of treatment tend to have a deficiency of vitamin D3, and obtain benefit from a vitamin D3 supplement, given either as an intramuscular injection or as an oral dose.

Further, a recent study dealing with patients with diabetic neuropathy found that treatments with daily oral doses of vitamin D3 resulted in a significant reduction in the diabetic neuropathic pain.

However, none of the studies carried out to date suggest that vitamin D3 would have any anti-inflammatory and/or anaesthetic or pain relieving properties when applied externally.

The only known treatment in which vitamin D3 is applied transdermally is a treatment for psoriasis, in which a cream containing the active form of vitamin D3 (calcitriol) is used. However, this cream is ineffective for the relief of neurogenic inflammation or neuropathic pain.

BRIEF DESCRIPTION OF THE DRAWINGS

By way of example only, preferred embodiments of the present invention are described with reference to the accompanying drawings, in which.

In the visual analogue scale: 0=no pain
10=worst imaginable pain

DETAILED DESCRIPTION OF PREFERRED EMBODIMENTS

A cream was prepared using a known pharmaceutical cream base plus 12,000 IU/gram powdered vitamin D3 in the form of cholecalciferol (25 (OH) D3). The cream was designed to be suitable for transdermal application by massaging into the skin.

EXAMPLE 1

Patient 1—History: MM, age 46, female, elite masters middle distance runner with 2-month history of right inferior heel pain treated initially with subcutaneous prolotherapy, complicated by infection, complaining of inability to run, difficulty walking, and pain at rest. Past history of bilateral peripatellar pain treated with failed surgical decompression, Achillodynia.

Figure 1:
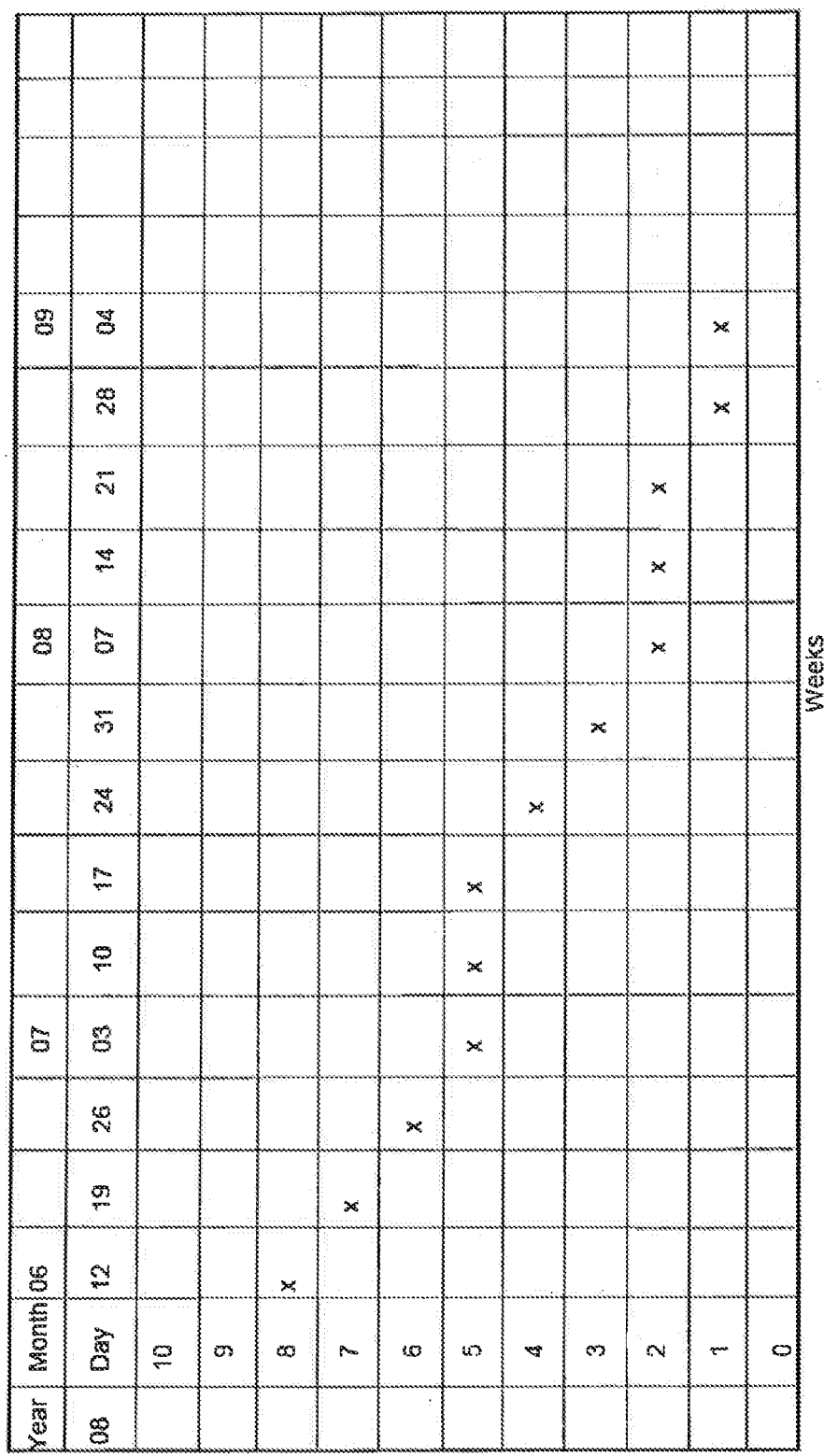
FIG. 1 is a visual analogue scale diagram showing progress of pain relief for Patient 1.

The patient applied the cream by massaging the cream into the painful area twice a day and after any activity, with the massaging followed by the application of heat where possible. This procedure was followed until all pain and tenderness had disappeared from the area. The treatment was continued for three months, and an assessment of pain was recorded every seven days, as shown in FIG. 1. Over this period, the pain reduced from a severe pain to very little pain, with the pattern of pain reduction being a period of steady decrease of pain followed by a plateau, then a further steady decrease followed by another plateau. It is notable that the patient has since continued to run and is pain-free, although continuing to use the cream.

EXAMPLE 2

Patient 2—History: JF, age 24, female, fitness trainer with 8-month history of left inferior heel pain, complaining of inability to run, difficulty walking, affecting work. Has prior treatment with physiotherapy and podiatry without effect. Past history of bilateral Osgood Schlatter Disease, right medial shin splints and peripatellar pain.

Figure 2:
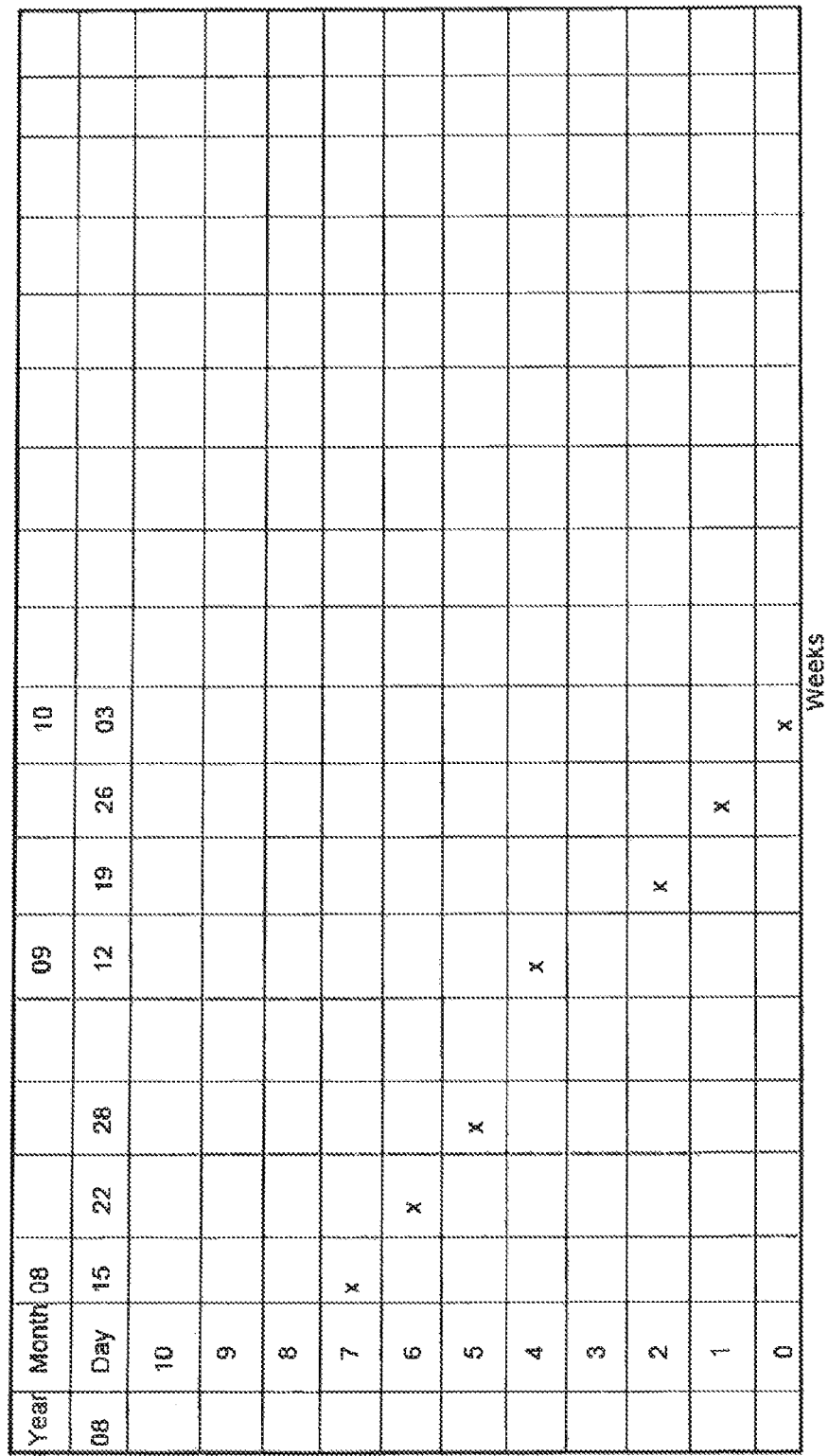
FIG. 2 is a visual analogue scale diagram showing progress of pain relief for Patient 2.

The patient applied the cream by massaging the cream into the painful area twice a day and after any activity, with the massaging followed by the application of heat where possible. This procedure was followed until all pain and tenderness had disappeared from the area. The treatment was continued for two months:—as shown in FIG. 2, over this period the pain steadily diminished from severe pain to no pain. This patient is still using the cream, and continues to run with no pain.

The patients from Examples 1 and 2 were monitored for serum vitamin D levels at the end of treatment; both showed normal levels.

EXAMPLE 3

A total of 14 patients, all suffering from recalcitrant inferior heel pain (plantar fasciitis) were studied over a period of several months. The patients consisted of three males with a mean age of 56 (range 50 to 60) and 11 females with a mean age of 44 (range 23 to 61).

Inferior heel pain (plantar fasciitis) is a difficult to treat condition, causing high levels of pain and disability for up to four years in one prospective study of 100 patients (BMJ Clinical Evidence Concise June 2006)

The underlying cause of inferior heel pain is postulated to be due to chronic neurogenic inflammation of the distal Tibial nerves branches known as the medial cutaneous calcaneal nerves.

All patients in this study had received prior treatment including physiotherapy, cortison injections and podiatry with taping and orthotics without benefit.

The patients were treated with a cream consisting of a known cream base of a type suitable for transdermal applications of medication to which had been added vitamin D3 in oil base form, at a concentration of 40,000 IU/gram. The cream was gently massaged into the skin over the inflamed portion, at least twice a day. Ten of the 14 patients were treated with the vitamin D3 cream only; four of the patients used the vitamin D3 cream in combination with weekly prolotherapy (injections of 20% glucose, 0.1% lignocaine). All patients were monitored at intervals for blood levels of vitamin D3; all levels were normal.

Figure 3:
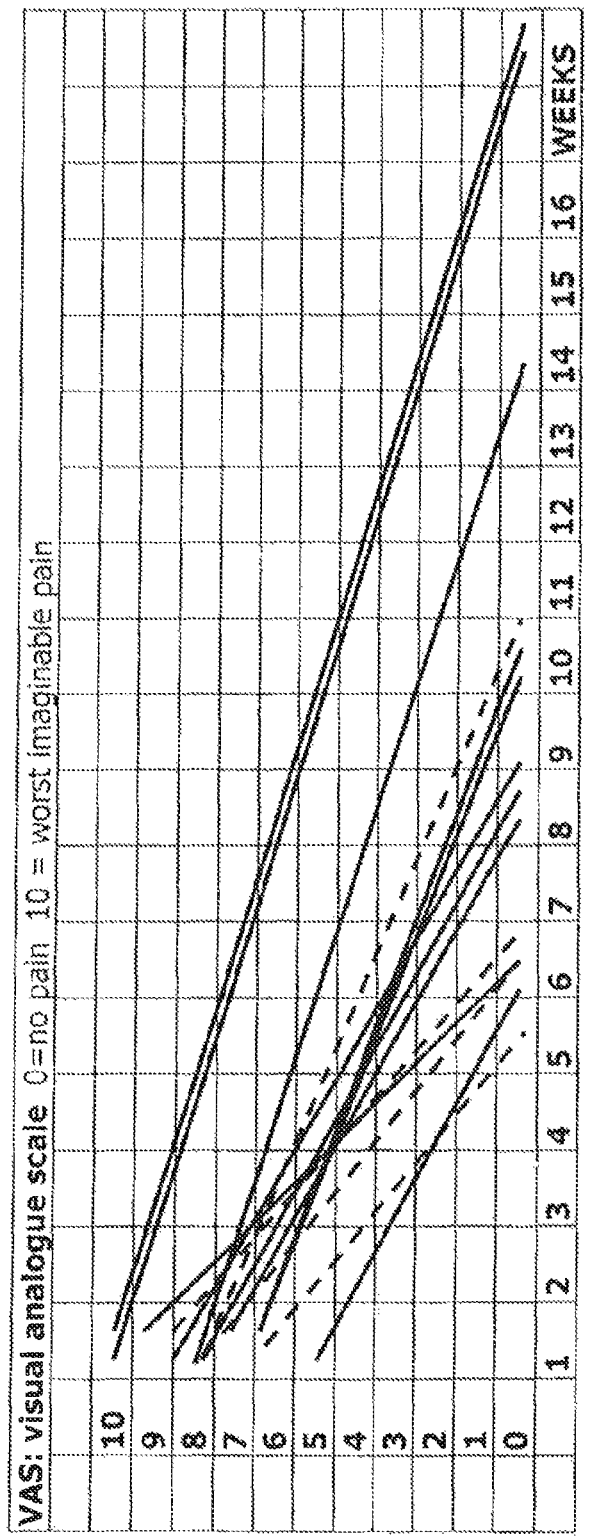
FIG. 3 is a visual analogue scale diagram showing the results of a one-year clinical audit on a number of patients.

Over the study period shown, all patients responded to the treatment with a complete recovery, with only one recorded relapse, and no adverse reactions were observed. The progress of the treatment is shown in FIG. 3 which shows the visual analogue scores for pain, graphed against time. The solid lines represent the cases treated with vitamin D3 cream only; the broken lines show the four cases treated with the combination of prolotherapy and vitamin D3 cream. FIG. 3 shows that there was little difference in outcome between the two treatments, and also shows that there was a strong correlation between initial pain scores and the length of treatment needed:—patients with high initial pain scores required a longer treatment period. However, there was a consistent and high response rate to the treatment with vitamin D3 cream alone.

Further testing on individual cases indicates that the medicament of the present invention is successful in relieving a wide range of forms of neurogenic inflammation and neuropathic pain, including peripheral neuropathic pain. The cream has been successful in relieving all of the following conditions:—plantar fascia, tennis elbow, golfers elbow, knee pain, Achilles tendon pain, neck pain (whiplash injury) low back pain, chronic exertional compartment syndrome, osteo arthritis symptoms of hand and fingers, fibromyalgia pains, hip pains and shoulder pains, contact dermatitis (especially contact dermatitis caused by cement/concrete and by Diesel), acute contusions, sprains and strains, purigo, first-degree burns (including sunburn), chilblains and shingles. In all cases, the condition is treated simply by massaging the cream into the affected area of skin. Many sprains and strains and other injuries causing neuropathic pain can become a cause of chronic pain, and the medicament of the present invention is particularly valuable in that it can be used to treat such pain quickly and effectively, thus preventing the neurogenic inflammation from becoming chronic and hence causing chronic pain.

Whenever the medicament of the present invention has been used, the levels of vitamin D3 in the user's blood have been monitored by a series of regular blood tests and it is interesting that in all cases so far, there have been no significant increases of vitamin D3 levels in the user's blood as a result of the use of the medicament.

The invention claimed is:

1. A method for treating at least one selected from the group consisting of neurogenic inflammation, neuropathic pain, and combinations thereof, said method comprising the step of transdermally administering a composition comprising calciol (cholecalciferol) to a subject in need thereof.

2. The method as claimed in claim 1, wherein the composition further comprises a carrier medium suitable for transdermal application, in which calciol (cholecalciferol) is dispersed or dissolved.

3. The method as claimed in claim 2, wherein the carrier medium is selected from the group consisting of: aqueous-based cream, massaging oil, gel base, ointment, patches, impregnated sheet material, pessaries and suppositories.

4. The method as claimed in claim 1, wherein the calciol (cholecalciferol) is present in a concentration in the range of 5000 IU/gram to 100,000 IU/gram.

5. The method as claimed in claim 1, wherein the calciol (cholecalciferol) is present in a concentration in the range of 5000 IU/gram to 200,000 IU/gram.

6. The method as claimed in claim 2, wherein the carrier medium is selected from the group consisting of aqueous-based cream, massaging oil, gel base, ointment, patches, impregnated sheet material, pessaries, suppositories, aerosol sprays, non-aerosol sprays and combinations thereof.

* * * * *